United States Patent
Jones et al.

(10) Patent No.: US 8,867,031 B2
(45) Date of Patent: Oct. 21, 2014

(54) ANESTHESIA VAPORIZER SYSTEM

(75) Inventors: Michael Eric Jones, Madison, WI (US); Kenneth J. Kuehl, Madison, WI (US)

(73) Assignee: General Electric Company, Schenectady, NY (US)

( * ) Notice: Subject to any disclaimer, the term of this patent is extended or adjusted under 35 U.S.C. 154(b) by 738 days.

(21) Appl. No.: 13/162,709

(22) Filed: Jun. 17, 2011

(65) Prior Publication Data

US 2012/0318264 A1    Dec. 20, 2012

(51) Int. Cl.
*G01C 9/18* (2006.01)
*A61M 16/18* (2006.01)
*A61M 16/01* (2006.01)
*A61M 16/10* (2006.01)
*A61M 16/00* (2006.01)

(52) U.S. Cl.
CPC .............. *A61M 16/01* (2013.01); *A61M 16/104* (2013.01); *A61M 16/1075* (2013.01); *A61M 16/18* (2013.01); *A61M 16/109* (2013.01); *A61M 2016/0039* (2013.01); *A61M 2202/0208* (2013.01); *A61M 2202/0283* (2013.01); *A61M 2205/3306* (2013.01); *A61M 2205/3389* (2013.01); *A61M 2205/50* (2013.01)
USPC ................. 356/249; 128/203.12; 128/203.14; 141/95

(58) Field of Classification Search
CPC ..... A61M 16/00; A61M 16/10; A61M 16/01; A61M 16/81; A61M 15/00; A61D 7/04; G01N 21/55; G01N 21/59
USPC ........ 356/440, 244, 246; 128/203.12, 203.14, 128/203.15, 203.22, 204.16; 141/95, 198, 141/2, 18
See application file for complete search history.

(56) References Cited

U.S. PATENT DOCUMENTS

| | | | |
|---|---|---|---|
| 4,998,022 A * | 3/1991 | Tregay | 250/577 |
| 6,422,073 B1 * | 7/2002 | Krahbichler et al. | 73/293 |
| 8,365,724 B2 * | 2/2013 | Bottom | 128/203.14 |
| 2008/0236580 A1 * | 10/2008 | Shang et al. | 128/203.16 |
| 2011/0102796 A1 * | 5/2011 | Shang et al. | 356/436 |
| 2011/0315139 A1 * | 12/2011 | Mashak | 128/203.14 |
| 2013/0255676 A1 * | 10/2013 | Kuehl et al. | 128/203.12 |

FOREIGN PATENT DOCUMENTS

GB    WO 92/19305    * 11/1992

* cited by examiner

Primary Examiner — Hoa Pham

(57) ABSTRACT

An anesthetic vaporizer system is disclosed herein. The anesthetic vaporizer system may include a sump adapted to retain an anesthetic agent. The anesthetic vaporizer system may also include a level sensor disposed at least partially within the sump. The level sensor is configured to generate an optical beam, and to estimate the amount of anesthetic agent within the sump based on a measured characteristic of the optical beam.

15 Claims, 3 Drawing Sheets

US 8,867,031 B2

ANESTHESIA VAPORIZER SYSTEM

FIELD OF THE INVENTION

This disclosure relates generally to an anesthesia vaporizer system. This disclosure relates more particularly to an anesthesia vaporizer system with an anesthetic agent level sensor.

BACKGROUND OF THE INVENTION

An anesthesia system may be implemented to deliver a predetermined dosage of anesthetic agent to a patient. The anesthesia system may be pneumatically connected to a vaporizer. Conventional vaporizers comprise a sump adapted to retain a liquid anesthetic agent, and a vaporization chamber adapted to convert the liquid anesthetic agent into a gas. The gaseous anesthetic agent is inhaled into the patient's lungs to produce an effect such as pain management, unconsciousness, preventing memory formation, and/or paralysis.

One problem with conventional vaporizers is that it is difficult to accurately assess the amount of anesthetic agent remaining within the sump.

BRIEF DESCRIPTION OF THE INVENTION

The above-mentioned shortcomings, disadvantages and problems are addressed herein which will be understood by reading and understanding the following specification.

In an embodiment, an anesthetic vaporizer system includes a sump adapted to retain an anesthetic agent. The anesthetic vaporizer system also includes a level sensor disposed at least partially within the sump. The level sensor is configured to generate an optical beam, and to estimate the amount of anesthetic agent within the sump based on a measured characteristic of the optical beam.

In another embodiment, an anesthetic vaporizer system includes a sump adapted to retain an anesthetic agent, and a level sensor disposed at least partially within the sump. The level sensor includes an emitter adapted to emit an optical beam, a receiver, and a reflector. The reflector is configured to redirect at least a portion of the optical beam toward the receiver. The anesthetic vaporizer system also includes a controller operatively connected to the level sensor. The controller is configured to estimate the amount of the anesthetic agent within the sump based on a measured characteristic of the optical beam.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
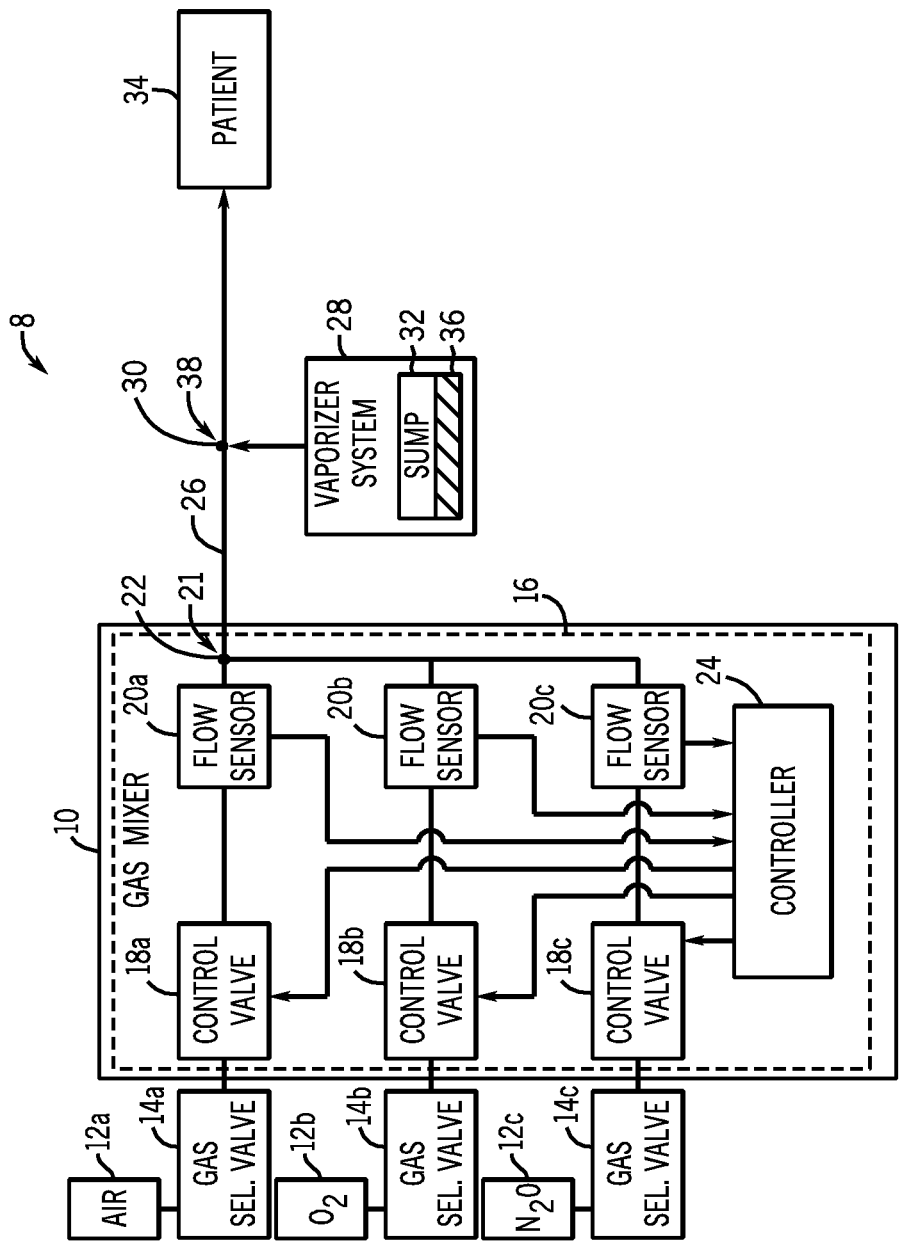
FIG. 1 is a schematic representation of an anesthesia system in accordance with an embodiment.

Referring to FIG. 1, an anesthesia system 8 is schematically depicted in accordance with one embodiment. The anesthesia system 8 includes an anesthesia machine 10, a plurality of gas storage devices 12a, 12b and 12c, and an anesthetic vaporizer system 28. The anesthesia machine 10 is shown for illustrative purposes and it should be appreciated that other types of anesthesia machines may alternately be implemented. In a typical hospital environment, the gas storage devices 12a, 12b and 12c are centrally located storage tanks configured to supply medical gas to multiple anesthesia machines and multiple hospital rooms. The storage tanks are generally pressurized to facilitate the transfer of the medical gas to the anesthesia machine 10.

The gas storage devices 12a, 12b and 12c will hereinafter be described as including an air tank 12a, an oxygen (O2) tank 12b, and a nitrous oxide (N2O) tank 12c, respectively, however it should be appreciated that other storage devices and other types of gas may alternatively be implemented. The gas storage tanks 12a, 12b and 12c are each connected to one of the gas selector valves 14a, 14b, and 14c, respectively. The gas selector valves 14a, 14b and 14c may be implemented to shut off the flow of medical gas from the storage tanks 12a, 12b and 12c when the anesthesia machine 10 is not operational. When one of the gas selector valves 14a, 14b and 14c is opened, gas from a respective storage tank 12a, 12b and 12c is transferred under pressure to the anesthesia machine 10.

The anesthesia machine 10 includes a gas mixer 16 adapted to receive medical gas from the storage tanks 12a, 12b and 12c. The gas mixer 16 includes a plurality of control valves 18a, 18b and 18c that are respectively connected to one of the gas selector valves 14a, 14b and 14c. The gas mixer 16 also includes a plurality of flow sensors 20a, 20b and 20c that are each disposed downstream from a respective control valve 18a, 18b, and 18c. After passing through one of the control valves 18a, 18b and 18c, and passing by one of the flow sensors 20a, 20b and 20c, the individual gasses (i.e., air, O2 and N2O) are combined to form a carrier gas 21 at the carrier gas outlet 22.

The control valves 18a, 18b and 18c and the flow sensors 20a, 20b and 20c are each connected to a controller 24. The controller 24 is configured to operate the control valves 18a, 18b and 18c in a response to gas flow rate feedback from the flow sensors 20a, 20b and 20c. Accordingly, the controller 24 can be implemented to maintain a selectable flow rate for each gas (i.e., air, O2 and N2O) such that the carrier gas 21 at the carrier gas outlet 22 comprises a selectable ratio of air, O2 and N2O. The carrier gas 21 flows to a pneumatic circuit 26.

A vaporizer system 28 comprises a sump 32 adapted to retain a liquid anesthetic agent 36. The vaporizer system 28 converts the liquid anesthetic agent 36 into a vaporized anesthetic agent 38. The vaporizer system 28 introduces the vaporized anesthetic agent 38 into the pneumatic circuit 26 at an inlet 30. The vaporized anesthetic agent 38 mixes with the carrier gas 21 and is delivered to a patient 34. Although the vaporizer system 28 is schematically depicted as being a separate component of the anesthesia system 8, it should be appreciated that it may alternatively be incorporated into the design of the anesthesia machine 10.

Figure 2:
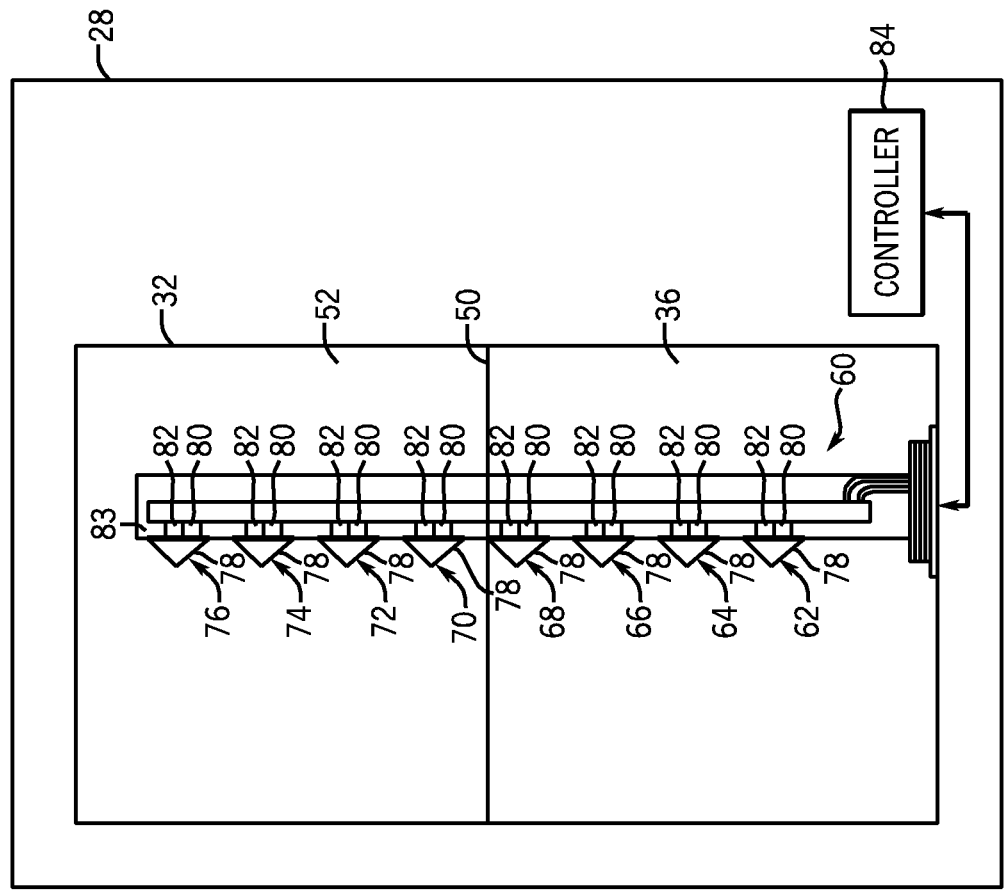
FIG. 2 is a schematic representation of a vaporizer system in accordance with an embodiment.

Referring to FIG. 2, a detailed schematic representation of the vaporizer system 28 is shown in accordance with an embodiment. As previously described the vaporizer system 28 comprises a sump 32. The sump 32 may comprise a first volume of anesthetic agent in the liquid phase 36 disposed below the liquid level line 50, and a second volume of anesthetic agent in the gas phase 52 disposed above the liquid level line 50. It should be appreciated that delivery of anesthetic agent to the patient 34 (shown in FIG. 1) has the effect of diminishing the volume of anesthetic agent in the liquid phase 36 and increasing the volume of anesthetic agent in the gas phase 52. It would be desirable to know with precision how much liquid anesthetic agent remains in the sump 32 so that, for example, the sump can be refilled proactively and/or during an optimally convenient interval.

The vaporizer system 28 comprises a level sensor 60 disposed at least partially within the sump 32. The level sensor 60 may be configured to precisely assess the amount of liquid anesthetic agent 36 within the sump 32. The level sensor 60 will now be described in more detail in accordance with an embodiment.

The level sensor 60 may comprise a plurality of discrete optoelectronic devices and in some embodiments may therefore be referred to as an optoelectronic level sensor. The depicted embodiment schematically shows eight vertically aligned optoelectronic devices 62-76. It should be appreciated that alternate optoelectronic device quantities and configurations may be envisioned.

The optoelectronic devices 62-76 may each comprise a reflector 78, an emitter 80 and a receiver 82. The reflectors 78 are schematically depicted in accordance with an embodiment as comprising a prism. It should, however, be appreciated that the reflectors 78 may comprise any device adapted to reflect or redirect an optical beam such as, for example, a minor. The emitters 80 may be configured to emit an optical beam toward a respective reflector 78. The receivers 82 may be configured to receive an optical beam from a respective reflector 78, and may be further configured to measure the intensity of the received optical beam.

The level sensor 60 may comprise a housing 83. The material and design considerations for the housing 83 are important to the precise operation of the level sensor 60. It should be appreciated that the housing 83 should adequately protect the level sensor 60 components from temperatures and pressures within the sump 32. The housing 83 should also minimize interference with the transmission of the optical beam from the emitters 80 to the receivers 82. Extensive research has indicated that a polyphenylsulfone material provides adequate component protection, and that a transparent polyphenylsulfone material does not significantly interfere with optical beam transmission.

The vaporizer system 28 may comprise a controller 84. The vaporizer system 28 may alternatively be operatively connected to a remotely located controller. The controller 84 may be operatively connected to the emitters 80, and be configured to control the operation of the emitters 80. The controller 84 may also be operatively connected to the receivers 82, and be configured to receive data from the receivers 82. While depicted as being disposed outside the sump 32 in accordance with an embodiment, it is envisioned that the controller 84 may implemented inside the sump 32 and/or integrated into the level sensor 60.

Figure 3:
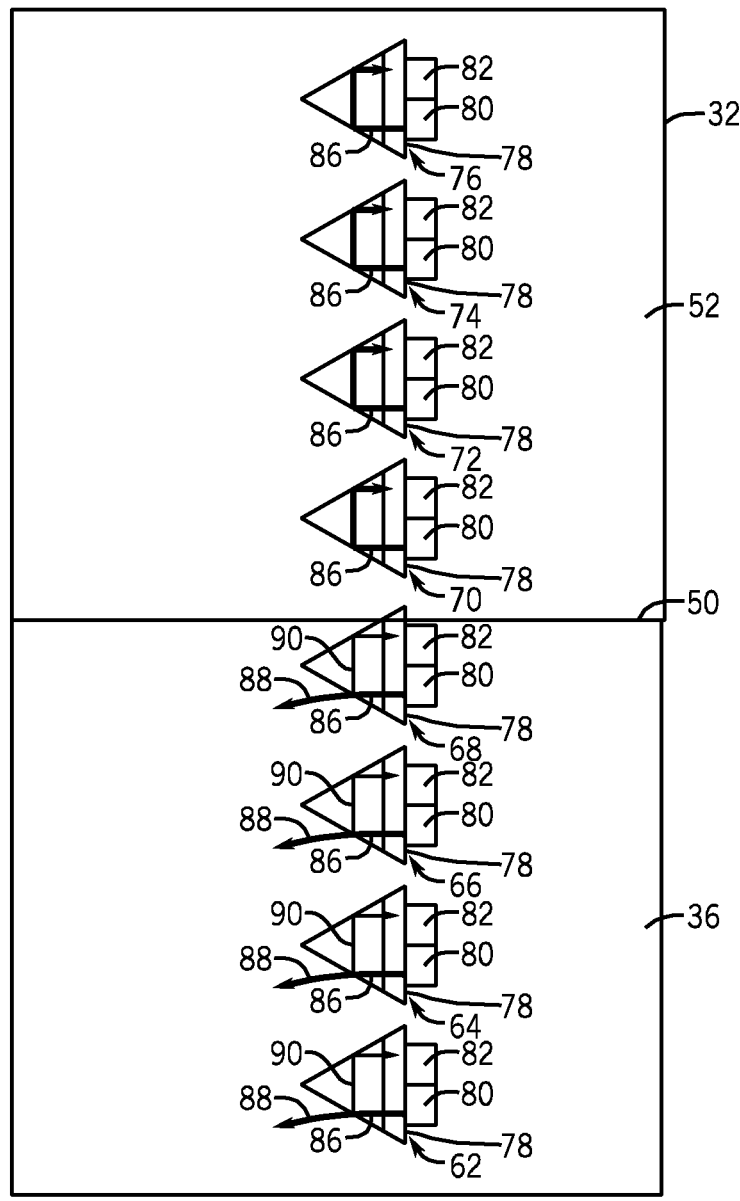
FIG. 3 is a schematic representation of a level sensor in accordance with an embodiment.

Referring to FIG. 3, the operation of the level sensor 60 will now be described in accordance with an embodiment. For illustrative purposes assume the liquid level line 50 is approximately in the vertical middle of the sump 32 such that the optoelectronic devices 62-68 are disposed within the liquid anesthetic agent 36 and the optoelectronic devices 70-74 are disposed within the gaseous anesthetic agent 52.

The emitters 80 are each configured to emit an optical beam 86 toward a corresponding reflector 78 at a known emission intensity. The optical beams 86 passing through the gaseous anesthetic agent 52 is generally uninterrupted as it is redirected by the reflector 78 back to a corresponding receiver 82. The receivers 82 are each configured to receive the optical beam 86 and measure its receipt intensity. The controller 84 (shown in FIG. 2) may be adapted to receive data comprising the received intensity from the receivers 82. The controller 84 may further be adapted to compare the receipt intensity of the optical beam 86 with its emission intensity.

It has been observed that the intensity of an optical beam 86 passing through a prism disposed in a gaseous anesthetic agent is only minimally diminished. If the controller 84 (shown in FIG. 2) compares and determines that the receipt intensity of a given optical beam 86 is approximately equal its emission intensity, it can be assumed that the corresponding optoelectronic device is disposed in gaseous anesthetic agent 52. Referring to the present exemplary embodiment, the controller 84 would identify optoelectronic devices 70-76 as being disposed in gaseous anesthetic agent 52.

It has been observed that the intensity of an optical beam 86 passing through a prism disposed in liquid anesthetic agent is significantly diminished. This intensity reduction is attributable to the refraction of the optical beam 86 by the liquid anesthetic agent 36. As graphically depicted in FIG. 3 for the optoelectronic devices 62-68 disposed in liquid anesthetic agent 36, the emitted optical beam 86 is partially refracted such that the refracted portion 88 is diverted away from the receiver 82 and only the remainder portion 90 is transmitted to the receiver 82. It should be appreciated that the remainder portion 90 has a lower intensity than the emitted optical beam 86. If the controller 84 (shown in FIG. 2) compares and determines that the receipt intensity of a given optical beam 86 is substantially less than its emission intensity, it can be assumed that the corresponding optoelectronic device is disposed in liquid anesthetic agent 36. Referring to the present exemplary embodiment, the controller would identify optoelectronic devices 62-68 as being disposed in liquid anesthetic agent 36.

The controller 84 (shown in FIG. 2) can be configured to estimate the amount of liquid anesthetic agent 36 within the sump 32 based on an assessment of the number of optoelectronic devices disposed in the liquid anesthetic agent 36. Referring to the present example, the controller 84 could estimate that the sump 32 is half full based on the previously described assessment that half of the optoelectronic devices 62-76 are disposed in liquid anesthetic agent 36.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An anesthetic vaporizer system comprising:
   a sump adapted to retain an anesthetic agent; and
   a level sensor disposed at least partially within the sump, said level sensor comprising a transparent polyphenylsulfone housing, the level sensor configured to generate an optical beam and to estimate the amount of anesthetic agent within the sump based on a measured characteristic of the optical beam.

2. The anesthetic vaporizer system of claim 1, wherein the level sensor is an optoelectronic level sensor.

3. The anesthetic vaporizer system of claim 2, wherein the optoelectronic level sensor comprises a reflector.

4. The anesthetic vaporizer system of claim 3, wherein the reflector comprises a prism.

5. The anesthetic vaporizer system of claim 3, wherein the optoelectronic level sensor is configured to direct the optical beam toward the reflector.

6. The anesthetic vaporizer system of claim 5, wherein the optoelectronic level sensor comprises a receiver configured to receive at least a portion of the optical beam from the reflector.

7. The anesthetic vaporizer system of claim 6, wherein the receiver is adapted to measure the intensity of said at least a portion of the optical beam.

8. The anesthetic vaporizer system of claim 2, wherein the optoelectronic level sensor is configured to estimate the amount of the anesthetic agent within the sump based on a measured intensity of the optical beam.

9. An anesthetic vaporizer system comprising:
a sump adapted to retain an anesthetic agent;
a level sensor disposed at least partially within the sump, said level sensor comprising:
a transparent polyphenylsulfone housing;
an emitter adapted to emit an optical beam;
a receiver; and
a reflector configured to redirect at least a portion of the optical beam toward the receiver; and
a controller operatively connected to the level sensor, said controller configured to estimate the amount of the anesthetic agent within the sump based on a measured characteristic of the optical beam.

10. The anesthetic vaporizer system of claim 9, wherein the receiver is adapted to measure the intensity of the optical beam.

11. The anesthetic vaporizer system of claim 10, wherein the controller is configured to estimate the amount of the anesthetic agent within the sump based on the intensity of the optical beam measured by the receiver.

12. The anesthetic vaporizer system of claim 10, wherein the controller is configured to estimate the amount of the anesthetic agent within the sump based on a comparison of the intensity of the emitted optical beam with the intensity of the optical beam measured by the receiver.

13. The anesthetic vaporizer system of claim 9, wherein the emitter comprises a plurality of emitters collectively adapted to emit a plurality of optical beams, the receiver comprises a plurality of receivers, and the reflector comprises a plurality of reflectors.

14. The anesthetic vaporizer system of claim 13, wherein the controller is configured to estimate the amount of the anesthetic agent within the sump based on a measured characteristic of each of the plurality of optical beams.

15. The anesthetic vaporizer system of claim 9, wherein the reflector comprises a prism.

* * * * *